United States Patent [19]

Barri et al.

[11] Patent Number: 5,126,502
[45] Date of Patent: Jun. 30, 1992

[54] PROCESS FOR DEHYDROGENATION OF $C_2$-$C_{10}$ PARAFFIN TO YIELD ALKENE PRODUCT

[75] Inventors: Sami A. I. Barri, Berkshire; Rabaab Tahir, Middlesex, both of England

[73] Assignee: British Petroleum Company p.l.c., London, England

[21] Appl. No.: 377,986

[22] Filed: Jul. 11, 1989

[30] Foreign Application Priority Data

Jul. 14, 1988 [GB] United Kingdom ............... 8816722

[51] Int. Cl.$^5$ .............................................. C07C 5/333
[52] U.S. Cl. .................................. 585/660; 585/661
[58] Field of Search ............... 585/660, 654, 658, 661

[56] References Cited

U.S. PATENT DOCUMENTS

| | | | |
|---|---|---|---|
| 4,020,011 | 4/1977 | Nishikawa | 252/441 |
| 4,438,288 | 3/1984 | Imai et al. | 585/629 |
| 4,458,098 | 7/1984 | Antos | 585/660 |
| 4,538,017 | 8/1985 | Butler et al. | 585/660 |
| 4,665,267 | 5/1987 | Barri | 585/660 |
| 4,795,732 | 1/1989 | Barri | 502/223 |

FOREIGN PATENT DOCUMENTS

| | | |
|---|---|---|
| 0035807 | 9/1981 | European Pat. Off. . |
| 0124998 | 11/1984 | European Pat. Off. . |
| 0212850 | 3/1987 | European Pat. Off. . |
| 0220525 | 5/1987 | European Pat. Off. . |
| 2516913 | 10/1975 | Fed. Rep. of Germany . |
| 2594711 | 8/1987 | France . |
| 1366334 | 9/1974 | United Kingdom . |
| 2162534 | 2/1986 | United Kingdom . |

OTHER PUBLICATIONS

Inui et al., "Effective Conversion of Paraffins", Innovations in Zeolitic Materials Science, 37 (1988) 487–494.

*Primary Examiner*—W. J. Shine
*Assistant Examiner*—Douglas J. McGinty

[57] ABSTRACT

A catalyst which comprises zinc, together with an effective amount of a platinum group metal on a support which is a material having the silicalite structure, the framework of said material consisting essentially of silicon and oxygen atoms or of silicon, zinc and oxygen atoms. There is also provided a process for the dehydrogenation of a $C_2$ to $C_{10}$ paraffin to yield an alkene product which process comprises contacting the paraffin under dehydrogenation conditions with a catalyst according to the invention.

12 Claims, No Drawings

PROCESS FOR DEHYDROGENATION OF $C_2$-$C_{10}$ PARAFFIN TO YIELD ALKENE PRODUCT

The present invention relates to a process for catalytically dehydrogenating hydrocarbons, to a novel dehydrogenation catalyst and to a process for producing the dehydrogenation catalyst.

Dehydrogenation is an important commercial process because of the great demand for olefins for the manufacture of a wide variety of chemical products such as detergents, high octane gasolines, pharmaceuticals, plastics, synthetic rubbers and many other chemical products.

To be commercially successful a dehydrogenation catalyst must satisfy at least three requirements, namely high activity, high selectivity and good stability. Activity is a measure of the catalyst's ability to convert dehydrogenatable hydrocarbons into products at a specified severity level, the severity level being a measure of the reaction conditions, i.e. temperature, pressure contact time etc, employed. Selectivity is a measure of the catalyst's ability to convert dehydrogenatable hydrocarbons into a desired product or products relative to the amount of hydrocarbon charged or converted. Stability is a measure of the rate of change with time of the activity and selectivity factors.

Heterogeneous catalysts comprising platinum group metals for the dehydrogenation of liquid or gaseous hydrocarbons have been previously described. Representative of the prior art relating to platinum group metal catalysts are U.S. Pat. Nos. 3,531,543; 3,745,112; 3,892,657; 3,909,451; 4,101,593; 4,210,769; 4,329,258; 4,363,721; 4,438,288; 4,458,098; and British Patent No. 1,499,297. Generally, in addition to the platinum group metal, there is employed a porous support and an additional component specifically selected for the purpose of improving the activity and/or selectivity and/or stability of the catalyst. The additional component is typically an alkali metal or an alkaline earth metal. A large number of porous supports are reported. These include (1) activated carbon, coke, or charcoal; (2) silica or silica gel, silicon carbide, clays and silicates; (3) ceramics, porcelain, crushed firebrick, bauxite; (4) refractory inorganic oxides such as alumina, titania, zirconia and the like; (5) crystalline zeolite silicates; (6) spinels; and (7) combinations of the foregoing. U.S. Pat. No. 4,438,288 describes a dehydrogenation process employing, as catalyst, a platinum group metal and an alkali or alkaline earth component, on a porous support material. Amongst the porous support materials disclosed is silicalite.

EP-A-212,850 discloses that dehydrogenation catalysts comprising a platinum group metal supported on a silicalite and substantially free of an alkali and alkaline earth metal can exhibit not only a high activity and selectivity but also improved stability as compared with prior art catalysts. We have now found that catalysts of this type can be improved still further by the incorporation of zinc.

Accordingly, the present invention provides a catalyst which comprises zinc, together with an effective amount of a platinum group metal on a support which is a material having the silicalite structure, the framework of said material consisting essentially of silicon and oxygen atoms or of silicon, zinc and oxygen atoms. The invention further provides a process for the dehydrogenation of a $C_2$ to $C_{10}$ paraffin to yield an alkene product which process comprises contacting the paraffin under dehydrogenation conditions with a catalyst according to the invention.

The catalyst according to the invention is preferably substantially free of alkali and alkaline earth metals. Throughout this Specification, the term substantially free does not exclude trace amounts of materials that occur as impurities in ordinary commercially available materials.

The zinc contained in the catalyst according to the invention may be present entirely as part of the framework of the support. Alternatively, some or all of the zinc may be deposited on the surface and in the pores of the support. Preferably, at least some of the zinc is present in elemental form.

The amount of zinc present in the catalyst may vary widely. Preferably the catalyst contains from 0.05 to 20%, preferably from 0.1 to 15% by weight of zinc.

The platinum group metal may suitably be at least one of platinum, ruthenium, iridium, rhodium or palladium and is preferably platinum. The metal is preferably present, at least in part, in elemental form. The catalyst may suitably contain up to 10%, preferably up to 5%, even more preferably from 0.01 to 2% by weight of the platinum group metal.

Silicalite is one form of crystalline silica polymorph and the term silicalite has been designated by Union Carbide. Silicalite can exist in a number of different structural forms depending upon the route by which it is prepared. Thus, one form (silicalite I) is described in U.S. Pat. No. 4,061,724 which relates to a silica polymorph consisting of crystalline silica which after calcination in air at 600° C. for one hour has a characteristic X-ray powder diffraction pattern similar to that of ZSM-5. Another form (silicalite II) is described in a publication in Nature, 280, 664–665 (1979) by D. M. Bibby, N. B. Milestone and L. P. Aldridge. Structurally, silicalite II has the same relationship to ZSM-11 as silicalite I has to ZSM-5. It has been proposed that silicalite I and silicalite II represent extreme end members of the ZSM-5 and ZSM-11 types of aluminosilicate zeolite. These materials are designated as having the MFI and MEL structures, see the "Atlas of Zeolite Structure Types, Meier and Olson (1989). Materials having the silicalite structure and containing zinc in the framework are described by Ball et al, "Zinc and aluminium substitutions in MFI structures; synthesis, characterisation and catalysis", in New Developments in Zeolite Science Technology, Proceedings of 7th International Zeolite Conference, Ed. Murakami, Iijima and Ward, 1986. The materials utilisable as catalyst supports in the operation of the present invention should contain only minor amounts of impurities, such as aluminium and/or gallium, within the framework thereof, in addition to the silicon and optionally zinc comprising the bulk of the framework. In general, the silicalite should contain less than 1 mole of framework impurities per 100 moles of $SiO_2$. EP-A-212,850 contains a number of X-ray powder diffraction patterns of silicalite samples.

It is an advantage of the preferred catalyst as used in the process of the present invention that no additional alkali metal or alkaline earth metal components are necessary for the performance of the invention. The risk of side reactions, such as cracking, and oligomerisation as a result of the acidic nature of certain of the prior art co-metals is reduced without the need to incorporate alkali metals. Catalyst preparation is thereby simplified. For the same reason, the catalyst according to the invention is also preferably substantially free from other metal components. The catalyst may suitably be prepared by any of the known techniques for preparing catalysts. These include impregnation, precipitation or gelation. A suitable method, for example, comprises impregnating the support with a soluble thermally decomposable compound of zinc and with a soluble thermally decomposable compound of the platinum group metal. A mineral acid, for example nitric acid, may be added to the impregnation solution or solutions in order to facilitate better the dispersion of the metallic component. The zinc and the platinum group metal may be introduced together by impregnation with a single solution, or separately. If they are introduced separately, a preferred process comprises impregnating with a zinc-containing solution; calcining the resultant material; impregnating with a platinum group metal-containing solution; and re-calcining. If the support already contains zinc incorporated in its framework, then impregnation with only a source of a platinum group metal may be carried out.

The catalyst composition may if desired be sulphided and/or halogenated in known manner. It is, however, a major advantage of the catalysts of the invention that sulphiding is not necessary, and preferably the catalyst is substantially free from sulphur.

At some stage after impregnation it is normal to decompose thermally decomposable zinc and platinum group metal compounds and preferably to activate reductively the catalyst composition.

In another aspect, the present invention provides a process for the production of a catalyst according to the invention, which process comprises forming a hydrogel comprising water, a soluble source of zinc, a source of silica and an organic nitrogen-containing compound and thereafter crystallising the hydrogel at elevated temperature; the process also comprising incorporating a source of a platinum group metal before or after crystallisation of the hydrogel.

Of the platinum group metals, platinum is preferred. The metal may if desired be added to the gel in the form of a salt or complex thereof. Platinum, for example, may suitably be added in the form of tetramine platinum dihydroxide or dihalide, for example dichloride.

A source of zinc is added during preparation of the hydrogel. A salt or complex of zinc is preferred. Under these conditions, at least some of the zinc is incorporated into the framework of the material having the silicalite structure. The amount of zinc added is suitably such as to provide up to 20%, preferably up to 15%, by weight of zinc in the final catalyst composition.

Suitable sources of silica include, for example, sodium silicate, silica hydrosol, silica gel, silica sol and silicic acid. A preferred source of silica is an aqueous colloidal dispersion of silica particles. A suitable cdommercially available source of silica is LUDOX (Trade Mark) Colloidal Silica supplied by Du Pont.

The organic nitrogen-containing compound may suitably be an amine, for example diethylamine or 1,6-diaminohexane, an alkanolamine, for example diethanolamine, or a tetraalkyl ammonium compound, for example tetrapropylammonium hydroxide or tetrabutylammonium hydroxide.

In addition to water, the hydrogel may if desired contain an alcohol, for example methanol or ethanol.

The proportions in which the water, silica source and organic nitrogen-containing compound are present in the hydrogel are such as to form one of the structurally distinct forms of silicalite. These proportions are disclosed in the aforesaid U.S. Pat. No. 4,061,724 and the article in Nature, 280, 664-665 (1979), which are incorporated herein by reference. The amount of the platinum group metal source if used may suitably be such as to provide up to 10% by weight, preferably up to 5% by weight, even more preferably between 0.01 and 2% by weight of the platinum group metal in the final catalyst composition.

Crystallisation may suitably be effected at a temperature greater than 100° C., preferably in the range from 140° to 220° C. The pressure may suitably be autogenous, that is the pressure generated within a closed vessel at the temperature employed. The crystallisation period will depend upon a number of factors including the rate of stirring and the temperature. Typically, within the preferred temperature range the crystallisation period may suitably be from 1 to 4 days.

The catalyst may be recovered, suitably by filtration or centrifugation, and washed, suitably with water at a temperature in the range, for example, of from 15° to 95° C.

Finally, the catalyst composition is preferably activated, suitably by a thermal treatment, for the purpose of decomposing thermally decomposable compounds. The thermal treatment may suitably be effected in the presence of an inert gas, for example nitrogen, or air. Alternatively, or in addition, the catalyst may be reductively activated by heating in the presence of a reducing gas, for example hydrogen. It is possible to combine the thermal treatment and the reductive treatment into a single operation.

If a source of platinum group metal was not present during preparation of the hydrogel, this may be incorporated by impregnation before or after activation of the catalyst.

As regards the process of the invention, dehydrogenation conditions suitably comprise a temperature in the range from about 300° to 800° C. and a pressure in the range from 0.01 to 10 bar. Since the dehydrogenation of hydrocarbons is an endothermic reaction and conversion levels are limited by chemical equilibrium, it is desirable in order to achieve high conversion to operate at high temperatures and low hydrogen partial pressures. Under severe conditions it is difficult to maintain high activity and selectivity for long periods of time because undesirable side reactions such as aromatisation, cracking, isomerisation and coke formation increase. Reaction conditions within the aforesaid ranges should be chosen with regard to maximising activity, selectivity and stability.

The paraffin is preferably a $C_3$ to $C_6$ paraffin. Examples of suitable paraffinic hydrocarbons include ethane, propane, n-butane, isobutane, n-pentane, isopentane, n-hexane, 2-methylpentane, 3-methylpentane, 2,2-dimethylbutane, n-heptane and the like. The term paraffin is intended to include substituted paraffins for example ethyl benzene which upon dehydrogenation yields styrene.

A diluent may be employed in the process. Suitable diluents include hydrogen, steam, methane, ethane and carbon dioxide. Preferably however the process is carried out without a diluent. It is an advantage of the process of the invention that, in general, large volumes of hydrogen are not required in order to render the process effective.

The product from the process of the invention comprises dehydrogenated hydrocarbons, unconverted dehydrogenatable hydrocarbons and hydrogen. It is preferred to recover hydrogen from the product. The hydrogen so-obtained may be utilised elsewhere or recycled to the dehydrogenation process as diluent. Depending upon the use to which the dehydrogenated hydrocarbon is to be put, it may be separated from the unconverted dehydrogenatable hydrocarbon. The separated unconverted hydrocarbons may then be recycled to the process.

Water or a material decomposable to water under dehydrogenation conditions, for example an alcohol, aldehyde, ether or ketone, may be admixed with the dehydrogenatable hydrocarbon either continuously or intermittently if so desired.

The invention will now be further illustrated by reference to the following Examples.

In the Examples and Comparison Tests the terms used are defined as follows:

| | |
|---|---|
| WHSV ($h^{-1}$) = | Weight hourly space velocity which is the weight of feed fed per weight of catalyst per hour. |
| Feed Conversion (wt %) = | 100 - weight % of feed in the hydrocarbon products. |
| Selectivity to isobutene (wt %) = | Weight % of isobutene in the hydrocarbon products × 100 per unit Feed Conversion |
| Selectivity to propene (wt %) = | Weight % of propene in the hydrocarbon products × 100 per unit Feed Conversion |

EXAMPLE 1

Synthesis of Silicalite 600 grams of an aqueous solution containing 20% by weight tetrapropylammonium hydroxide (TPAOH) was added with stirring to 2000 grams of Ludox AS40 (Trade Mark, ex Dupont) containing 40% by weight silica (ammonia stabilised). The resultant hydrogel had the molar composition of:

4.4 TPAOH:1.4 $NH_3$:100 $SiO_2$:700 $H_2O$

The hydrogel was heated at 175° C. for 72 hours in a pressure vessel under autogenous pressure. The vessel was then cooled and the product was filtered, washed with distilled water dried at 100° C. The X-ray powder diffraction pattern showed that the product was silicalite-1 (MFI-type structure) as characterised in EP-A-0212850.

EXAMPLE 2

Treatment of Silicalite

The silicalite sample was calcined at 600° C. in air for 48 hours. It was then stirred in 20% by weight nitric acid (silicalite/solution=0.25 by weight) for 1 hour at room temperature, filtered, washed with distilled water, dried and calcined again at 600° C. for 16 hours.

EXAMPLE 3

Preparation of 0.5 wt % Pt/silicalite—Catalyst A 30 grams of the treated silicalite was mixed with 150 grams of an aqueous solution containing 0.27 gram of $Pt(NH_3)_4Cl_2.H_2O$. The mixture was then dried in a rotary evaporator under vacuum. The solid was then placed in an air oven at 100° C. for 10-15 minutes.

EXAMPLE 4

Preparation of 0.5 wt % Pt/4.0 wt % Zn/silicalite—Catalyst B

The treated silicalite (30 grams) was mixed with 150 grams of an aqueous solution containing 4.2 grams of $Zn(C_2H_3O_2)_2.2H_2O$ and the mixture was dried in a rotary evaporator under vacuum. The solid was then calcined at 550° C. in air for 16 hours. The Zn impregnated solid was mixed with 150 grams of aqueous solution containing 0.24 gram of $Pt(NH_3)_4Cl_2.H_2O$. The mixture was dried in a rotary evaporator under vacuum as above.

EXAMPLE 5

Preparation of Zincosilicate 90 grams of zinc sulphate ($ZnSO_4.7H_2O$) were dissolved in 300 grams of distilled water. Ammonia solution (25%) was added dropwise with stirring until the pH reached 6. The precipitate was filtered, washed with distilled water and dried on a Buchner filter for 1 hour. 40 grams of sodium hydroxide and the above precipitate were mixed with 400 grams of distilled water and the mixture was stirred for 15 minutes. 500 grams of tetrapropylammonium hydroxide (TPAOH) aqueous solution (containing 20 wt % TPAOH) was added with stirring followed by 700 grams of Ludox AS40 (Trade Mark, ex DuPont) (containing 40% by weight $SiO_2$). The hydrogel had a molar composition of:

1.60 $Na_2O$:1.57 TPAOH:ZnO:14.9 $SiO_2$:217 $H_2O$

The hydrogel was loaded into approximately 3 liter pressure vessel and stirred by rocking action at 175° C. for 4 days. At the end of this period the pressure vessel was cooled to ambient and the content was filtered, washed, and dried at 100° C. The dried product was examined by X-ray powder diffraction and shown to have the silicalite (MFI-type) structure.

A 50 gram sample of this dried zincosilicate was calcined at 550° C. in air for 18 hours to remove the organic content. It was then exchanged twice with 1 liter $NH_4NO_3$ solution (1M) for 1 hour at room temperature to replace sodium content by ammonium ions. The $NH_4$ exchanged zincosilicate was converted to the H-form by calcining at 550° C. for 18 hours in air to remove $NH_3$.

EXAMPLE 6

Preparation of 0.5 wt % Pt/zincosilicate—Catalyst C

The zincosilicate (38.9 grams) of Example 5 was mixed with 150 grams of distilled water and 0.35 gram of $Pt(NH_3)_4Cl_2.H_2O$ and the mixture was stirred and dried in a rotary evaporator under vacuum as above.

EXAMPLE 7

Catalyst Preparation and Activation

Catalysts A, B and C were activated as follows before testing. The catalysts as prepared in Examples 3, 4 and 6 were pressed at 14 tonnes pressure to form tablets and crushed and sieved to form 8 to 16 mesh (BSS) granules. The granules (approx. 5 cm³) were packed into a tubular quartz reactor which was 450 mm in length and 15 mm internal diameter. The reactor had a coaxial thermocouple well of approx. 3 mm outer diameter and the catalyst granules were sandwiched between two regions (each of 35 cm³) of inert beads.

Air (approx. 600 cm³/min) was passed over the catalyst and the temperature was raisd to 400° C. at the rate of 1.5° C./min and kept at 400° C. for at least 16 hours. The catalyst was then flushed with nitrogen and hydrogen was passed at 600 cm³/min. The temperature was then raised to the operating temperature at 1.5° C./min and kept at that temperature for at least 2 hours.

EXAMPLE 8

Catalyst Testing

The activated catalysts as described above were tested for the dehydrogenation of propane and/or isobutane in a continuous flow reactor. The results obtained and conditions used are given in the following Tables.

Table 1 shows the results obtained using a propane feedstock over prior art catalyst A, with and without sulphiding, and catalyst B according to the invention. It can be seen that all the catalysts were very stable with time. However, the catalyst according to the invention results in greater conversion of the feedstock than the prior art catalyst with or without sulphiding, and a greater selectivity than the sulphided prior art catalyst.

Table 2 shows the results obtained using an isobutane feedstock. Again, it can be seen that the catalysts B and C, according to the invention, produce much improved results over those obtained using the prior art catalyst A.

TABLE 1

DEHYDROGENATION OF PROPANE
Feed: 95% propane; 4.5% Ethane; 0.5% isobutane v/v
Pressure: atmospheric

| Catalyst | Time on Stream h | Temperature °C. | WHSV $h^{-1}$ | Conv.[1] % wt | Selectivity[2] % wt |
|---|---|---|---|---|---|
| A | 44 | 530 | 2.4 | 20 | 99 |
|   | 141 | 530 | 2.4 | 16 | 100 |
| A[3] | 79 | 570 | 2.2 | 23 | 82 |
|   | 621 | 570 | 2.2 | 23 | 96 |
| B | 51 | 555 | 3.0 | 27 | 100 |
|   | 123 | 555 | 3.0 | 25 | 99 |

[1] Conversion of propane
[2] Selectivity to propene
[3] 100 ppm $H_2S$ and $H_2$ ($H_2$/propane volume ratio = 0.5) added to feed

TABLE 2

DEHYDROGENATION OF ISO-BUTANE
Feed: isobutane
Pressure: atmospheric

| Catalyst | Temperature °C. | WHSV $h^{-1}$ | Feed Conversion % wt | Selectivity to isobutene % wt |
|---|---|---|---|---|
| A | 530 | 1 | 64.2 | 37.6 |
|   | 530 | 4 | 43.7 | 76.9 |
|   | 590 | 4 | 63.0 | 45.0 |
|   | 530 | 9 | 24.9 | 76.9 |
| B | 530 | 1 | 53.8 | 44.3 |
|   | 530 | 4 | 35.7 | 84.0 |
|   | 530 | 7 | 33.7 | 87.0 |
|   | 590 | 7 | 51.7 | 77.9 |
|   | 530 | 9 | 26.3 | 94.7 |
|   | 530[1] | 5 | 38.2 | 90.5 |
|   | 530[2] | 5 | 40.7 | 87.1 |
| C | 535 | 1 | 46.6 | 87.6 |
|   | 535 | 5 | 33.5 | 96.6 |
|   | 550[3] | 5 | 48.6 | 85.4 |

TABLE 2-continued

DEHYDROGENATION OF ISO-BUTANE
Feed: isobutane
Pressure: atmospheric

| Catalyst | Temperature °C. | WHSV $h^{-1}$ | Feed Conversion % wt | Selectivity to isobutene % wt |
|---|---|---|---|---|
|   | 570[3] | 5 | 55.6 | 85.5 |

[1] Time on stream = 100 hours
[2] Time on stream = 600 hours
[3] Catalyst held under $H_2$ flow for 48 hours at 535° C. before temperature was raised to 550° C. and then to 570° C.

EXAMPLE 9

Preparation of 0.5 wt % Pt/3 wt %/Zn/silicalite—Catalyst D 27 grams of the treated silicalite (as described in example 2) was mixed with 350 grams of an aqueous solution containg 2.7 grams of $Zn(C_2H_3O_2)_2.2H_2O$ and the mixture was dried in a rotary evaporator under vacuum. The solid was then placed in an air oven at 80 C. for 2 hours. The solid was then calcined at 500° C. in air for 16 hours. The zinc impregnated solid was mixed with 350 grams of aqueous solution containing 0.24 grams of $Pt(NH_3)_4Cl_2.H_2O$. The mixture was dried in a rotary evaporator under vacuum.

EXAMPLE 10

Preparation of 0.5 wt % Pt/1.5 wt % Zn/silicalite—Catalyst E

Catalyst E was prepared in the same way as described in Example 9, using sufficient zinc acetate dihydrate to enable a 1.5 wt % loading.

EXAMPLE 11

Catalyst Preparation and Activation

Both catalysts D and E were activated as follows prior to testing. The catalysts prepared in Examples 9 and 10 were pressed at 14 tonnes pressure to form tablets and crushed and sieved to form 8 to 16 mesh (BSS) granules. The granules (approx. 5 cm³) were packed into a tubular quartz reactor which was 450 mm in length and 15 mm internal diameter. The reactor had a coaxial thermocouple well of approximately 3 mm outer diameter and the catalyst granules were sandwiched between two regions (each of 35 cm³) of inert beads.

Catalyst D

Air (approx 600 cm³/min) was passed over the catalyst and the temperature was raised to 400 C. at 0.5 C./min for at least 16 hours. The catalyst was then flushed with nitrogen for 0.5 hour and hydrogen was passed at 375 cm³/min. The temperature was then raised to 540 C. at 0.5 C./min and kept at that temperature for at least 1 hour.

Catalyst E

Air (approx 600 cm³/min) was passed over the catalyst and the temperature was raised to 400 C. at 1.5 C./min for at least 16 hours. The catalyst was then flushed with nitrogen for 10 mins and hydrogen was passed over the catalyst. The temperature was then raised to 530 C. at 1.1 C./min and kept at that temperature for at least 0.5 hour.

Example 12

Catalyst testing

The activated catalysts described in Example 11 were tested for the dehydrogenation of propane and/or isobutane in a continuous flow reactor. The results obtained and conditions used are given in Tables 3 and 4.

TABLE 3

DEHYDROGENATION OF ISO-BUTANE
Catalyst: 0.5 wt % PT/3 wt % Zn/silicalite - Catalyst D
Feed: isobutane
WNSV: 4 h$^{-1}$

| Temperature | Feed Conversion wt % | Isobutene Selectivity wt % | Isobutene Yield wt % |
|---|---|---|---|
| 550 | 45.8 | 88.5 | 40.6 |
| 580 | 58.2 | 80.5 | 46.9 |

TABLE 4

DEHYDROGENATION OF PROPANE
Catalyst: 0.5 wt % Pt/1.5 wt % Zn/silcalite - Catalyst E
Feed: Propane/hydrogen (4:1 molar)
WHSV: 2.2 h$^{-1}$
Temperature: 570 C

| Time on stream h | Propane Conversion wt % | Propane Selectivity wt % | Propane Yield wt % |
|---|---|---|---|
| 480 | 33.8 | 91.1 | 30.8 |
| 796 | 34.1 | 90.5 | 30.9 |

EXAMPLE 13

Synthesis of silicalite-II/MEL type structure 53.5 grams of tetrabutylammonium hydroxide (TBAOH,40%) was added with stirring to 40.9 grams of distilled water. 11.0 grams of ammonia solution (25%) was added, followed by 94.5 grams of Ludox AS40 (Trade Mark, ex DuPont) containing 40% by weight silica (ammonia stabilised). The resulting mixture had the molar composition:

13.0 TBAOH:25.7 NH$_3$:100 SiO$_2$:1216 H$_2$O

The hydrogel was heated for 96 hours in a pressure vessel under autogenous pressure. As in example 1, the vessel was cooled and the contents were filtered, washed with distilled water and dried at 100 C. The X-ray powder diffraction showed that the product was silicalite-II (MEL-type structure) as shown in Table 5.

EXAMPLE 14

Treatment of silicalite-II

The silicalite sample produced in example 13 was acid washed by stirring in 10% by weight nitric acid (silicalite/solution=0.25 weight) for 1 hour at room temperature, filtered, washed with distilled water, dried at 100 C. for 1 hour and then calcined at 580 C. in air for 12 hours. The acid wash treatment was repeated.

EXAMPLE 15

Preparation of 0.5 wt % Pt/2.4 wt % Zn/silicalite-II

As in example 4, the treated silicalite (14.88 grams) produced in examples 13 and 14 was mixed in an aqueous mixture containing 1.25 grams of Zn(C$_2$H$_3$O$_2$)$_2$.2H$_2$O. The mixture was dried in a rotary evaporator under vacuum. The solid was then calcined in air at 550 C. for 16 hours. The Zn impregnated solid was mixed with an aqueous solution containing 0.13 grams of Pt(NH$_3$)$_4$Cl$_2$.H$_2$O. The mixture was dried in a rotary evaporator under vacuum as above. The resulting mixture had the X-ray powder diffraction pattern as shown in Table 6.

EXAMPLE 16

Catalyst preparation and activation

The product of example 15 underwent catalyst preparation and activation as in example 7.

EXAMPLE 17

Catalyst Testing

The catalyst activated as in example 16 was tested for the dehydrogenation of isobutane in a continuous flow reactor as in example 8. The results are shown in Tables 7 and 8.

TABLE 5

XRD OF SILICALITE II AS PREPARED IN EXAMPLE 13
Measured on a fixed-slit (¼ degree) X-ray diffractometer using copper k-alpha radiation.
Theta = Bragg angle; I = intensity of peak;
Io = intensity of strongest peak

| 2 Theta | d-spacing (Å) | 100 × I/Io |
|---|---|---|
| 7.88 | 11.22 | 53.42 |
| 8.77 | 10.08 | 46.52 |
| 11.81 | 7.49 | 4.22 |
| 12.43 | 7.11 | 1.50 |
| 13.14 | 6.73 | 3.00 |
| 13.73 | 6.45 | 1.16 |
| 14.54 | 6.09 | 4.61 |
| 14.73 | 6.01 | 6.76 |
| 15.80 | 5.60 | 3.85 |
| 17.17 | 5.16 | 1.41 |
| 17.63 | 5.03 | 3.36 |
| 19.17 | 4.63 | 4.34 |
| 20.28 | 4.38 | 8.48 |
| 22.12 | 4.01 | 3.16 |
| 23.06 | 3.85 | 100.00 |
| 23.85 | 3.73 | 33.61 |
| 24.28 | 3.66 | 8.27 |
| 25.45 | 3.50 | 3.89 |
| 26.15 | 3.41 | 3.26 |
| 26.59 | 3.35 | 5.39 |
| 27.99 | 3.19 | 1.20 |
| 29.11 | 3.07 | 5.06 |
| 29.84 | 2.99 | 7.95 |
| 31.16 | 2.87 | 1.33 |
| 32.00 | 2.79 | 0.97 |
| 33.62 | 2.66 | 0.59 |
| 34.23 | 2.62 | 2.12 |
| 35.09 | 2.56 | 1.05 |
| 35.72 | 2.51 | 2.12 |
| 35.95 | 2.50 | 2.28 |
| 37.36 | 2.41 | 1.50 |

TABLE 6

XRD OF 0.5 wt % Pt/2.4 wt % Zn/silicalite II
AS PREPARED IN EXAMPLE 15
Measured on a fixed-slit (¼ degree) X-ray diffractometer using copper k-alpha radiation.
Theta = Bragg angle; I = intensity of peak;
Io = intensity of strongest peak

| 2 Theta | d-spacing (Å) | 100 × I/Io |
|---|---|---|
| 7.94 | 11.13 | 100.0 |
| 8.84 | 9.99 | 57.3 |
| 11.91 | 7.43 | 0.61 |
| 12.53 | 7.06 | 14.25 |
| 13.23 | 6.69 | 3.77 |
| 13.82 | 6.40 | 1.51 |
| 14.83 | 5.97 | 10.65 |
| 15.45 | 5.73 | 1.30 |
| 15.92 | 5.56 | 5.92 |

TABLE 6-continued

XRD OF 0.5 wt % Pt/2.4 wt % Zn/silicalite II
AS PREPARED IN EXAMPLE 15
Measured on a fixed-slit (¼ degree) X-ray diffractometer using
copper k-alpha radiation.
Theta = Bragg angle; I = intensity of peak;
Io = intensity of strongest peak

| 2 Theta | d-spacing (Å) | 100 × I/Io |
| --- | --- | --- |
| 17.28 | 5.13 | 27.92 |
| 17.75 | 4.99 | 4.10 |
| 19.28 | 4.60 | 2.17 |
| 19.87 | 4.47 | 0.78 |
| 20.39 | 4.35 | 3.53 |
| 23.19 | 3.83 | 38.34 |
| 23.97 | 3.71 | 16.26 |
| 24.40 | 3.65 | 4.19 |
| 25.62 | 3.47 | 1.49 |
| 26.28 | 3.39 | 1.35 |
| 26.75 | 3.33 | 2.45 |
| 27.39 | 3.25 | 0.71 |
| 28.08 | 3.17 | 0.47 |
| 29.28 | 3.04 | 2.32 |
| 29.98 | 2.98 | 4.43 |
| 31.29 | 2.86 | 0.40 |
| 32.16 | 2.78 | 0.20 |
| 33.78 | 2.65 | 0.42 |
| 34.43 | 2.60 | 0.20 |
| 35.25 | 2.54 | 0.52 |
| 35.75 | 2.51 | 0.73 |
| 36.10 | 2.49 | 1.53 |
| 37.27 | 2.41 | 0.74 |
| 37.57 | 2.39 | 0.76 |

TABLE 7

DEHYDROGENATION OF ISOBUTANE
Catalyst: 0.5 wt % Pt/2.4 wt % Zn/ silicalite II
Feed: Isobutane
Temperature: 540 C
WHSV: 1 to 4 h$^{-1}$

| WHSV h$^{-1}$ | Isobutane Conversion wt % | Isobutene Selectivity wt % | Isobutene Yield wt % |
| --- | --- | --- | --- |
| 1 | 70.8 | 20.0 | 14.1 |
| 2 | 59.7 | 33.5 | 20.0 |
| 3 | 48.5 | 52.2 | 25.3 |
| 4 | 40.0 | 88.3 | 35.4 |

TABLE 8

DEHYDROGENATION OF ISOBUTANE
Catalyst: 0.5 wt % Pt/2.4 wt % Zn/ silicalite II
Feed: Isobutane
WHSV: 4 h$^{-1}$

| Temperature | Isobutane Conversion wt % | Isobutene Selectivity wt % | Isobutene Yield wt % |
| --- | --- | --- | --- |
| 540 | 40.0 | 88.3 | 35.4 |
| 550 | 46.2 | 88.4 | 40.9 |
| 560 | 52.0 | 84.6 | 44.0 |
| 570 | 57.7 | 81.7 | 47.2 |
| 580 | 63.4 | 78.5 | 49.8 |
| 590 | 64.2 | 81.0 | 52.0 |
| 600 | 69.1 | 74.4 | 51.4 |

We claim:

1. A process for the dehydrogenation of a $C_2$ to $C_{10}$ paraffin to yield an alkene product, which comprises contacting the paraffin under dehydrogenation conditions with a catalyst which comprises zinc, together with an effective amount of a platinum group metal on a support which is a material having the silicalite structure, the framework of said material consisting essentially of silicon and oxygen atoms or of silicon, zinc and oxygen atoms.

2. A process as claimed in claim 1, in which said conditions include the temperature range from 300° to 800° C.

3. A process as claimed in claim 2, in which the feedstock is a $C_3$ to $C_6$ paraffin.

4. A process as claimed in claim 1, in which the catalyst has been activated by thermal treatment prior to contact with the paraffin.

5. A process according to claim 1, in which said catalyst is substantially free from alkali and alkaline earth metals.

6. A process as claimed in claim 1, in which said catalyst contains from 0.1 to 15% by weight of zinc.

7. A process as claimed in claim 1, in which the platinum group metal is platinum.

8. A process as claimed in claim 1, in which the catalyst contains from 0.01 to 2% by weight of the platinum group metal.

9. A process as claimed in claim 5 in which said catalyst contains from 0.1 to 15% by weight of zinc.

10. A process as claimed in claim 9, in which the platinum group metal is platinum.

11. A process as claimed in claim 6, in which the platinum group metal is platinum.

12. A process as claimed in claim 5, in which the platinum group metal is platinum.

* * * * *